(12) United States Patent
Liou

(10) Patent No.: US 6,273,713 B1
(45) Date of Patent: Aug. 14, 2001

(54) PALATAL ADJUSTING DEVICE

(76) Inventor: Eric Jein-Wein Liou, No. 199, Tun-Hwa North Rd., Taipei (TW)

( * ) Notice: Subject to any disclaimer, the term of this patent is extended or adjusted under 35 U.S.C. 154(b) by 0 days.

(21) Appl. No.: 09/663,840

(22) Filed: Sep. 15, 2000

(51) Int. Cl.⁷ .................................................. A61C 3/00
(52) U.S. Cl. ................................................ 433/19; 433/21
(58) Field of Search ......................................... 433/19, 21

(56) References Cited

U.S. PATENT DOCUMENTS

| | | | |
|---|---|---|---|
| 4,382,783 | * 5/1983 | Rosenberg | 433/19 |
| 4,618,324 | * 10/1986 | Nord | 433/19 |
| 5,645,423 | * 7/1997 | Collins, Jr. | 433/19 |
| 5,846,074 | * 12/1998 | Klapper | 433/19 |
| 5,980,247 | * 11/1999 | Cleary | 433/19 |
| 6,074,207 | * 6/2000 | Coats | 433/19 |

* cited by examiner

Primary Examiner—John J. Wilson
(74) Attorney, Agent, or Firm—Dougherty & Troxell

(57) ABSTRACT

A palatal adjusting device includes an elastic means which has two arms in different directions engageable respectively with an upper barrel band and a lower barrel band mounted respectively on an upper molar and a lower molar. When a patient's mouth is closed, the elastic means will be compressed to produce an upward force or a forward force to push the upper jaw bone upward or forward for the upper teeth to have proper occlusal contact with the lower teeth.

7 Claims, 6 Drawing Sheets

PALATAL ADJUSTING DEVICE

FIELD OF THE INVENTION

This invention relates to a palatal adjusting device and particularly a palatal adjusting device to move the upper jaw bone upward and forward for the upper teeth to have proper occlusal contact with the lower teeth.

BACKGROUND OF THE INVENTION

Because of born defect or disease, some children have occlusion problem between the upper and lower teeth. FIG. 1 shows one of the cases in which the molars 1, 2 of the upper and low jaw may occlude properly, but the premolar 11, 21, canine and incisors 12, 22 of the upper and lower jaw cannot occlude properly and may result in a gap between the upper and lower teeth beyond the molars. It is not only unsightly, it also produces biting, chewing and digesting problem. To remedy this defect, one conventional treatment is to have a surgical operation to remove a slice of upper jaw bone which support the upper molars and to make the molars, premolars, canine and incisors have proper occlusal contact surface needed. It is a painful and expansive treatment.

There are other occasions in which patient's upper jaw bone is stepped behind the lower jaw bone and may result in no proper occlusal contact between the upper and lower front teeth. Then the upper jaw bone should be moved forward to remedy this defect. A conventional treatment is shown in FIG. 2. The upper molar 1 at both sides have a barrel band 13 mounted thereon. There is an anchor 14 located on a side wall of the barrel band 13 for fastening a steel wire 15. The steel wire 15 engages with a facial mask 3 which rests on patient's forehead and jaw. The steel wire 15 is subjected to a tension to pull the barrel band 13 forward. Then gradually the upper jaw bone will be pulled forward to mates with the lower jaw bone. It is a very troublesome and unconvenient treatment. The facial mask greatly interferes daily life and work of the patient. It can be done only a few hours daily, such as during sleep time at night. Its effectiveness is thus low and slow. All this begs for further improvement.

SUMMARY OF THE INVENTION

It is an object of this invention to provide a palatal adjusting device that can raise upper jaw bone for producing proper occlusal contact between the upper and lower teeth of a patient.

It is another object of this invention to provide a palatal adjusting device that can move upper jaw bone forward for producing proper occlusal contact between the upper and lower teeth of a patient.

It is a further object of this invention to provide a palatal adjusting device that is simply structured and small size and easy to use without surgical operation or bulky facial mask.

It is yet another object of this invention to provide a palatal adjusting device that may be used constantly day and night without patient's extra work or action, and may effectively adjust patient's upper jaw bone in a short period of time.

In one aspect, this invention includes an elastic means with two arms forming a selected angle. Each arms has an end engaged with a barrel band mounted respectively on an upper and a lower molar. When the patient closes the mouth, the elastic means will be compressed and produces a vertical force to push the upper jaw bone upward. Gradually the molar, premolar, canine and incisors of the upper jaw may be leveled and have occlusal contact with the lower teeth. The elastic means may be installed in patient's mouth easily and may be used constantly day and night to enhance treatment effect. In another aspect, the elastic means may have the two arms extended substantially linearly in opposite direction. Then when patient's mouth is closed, the elastic means will be compressed and produces a forward pulling force to move the barrel band in the upper jaw forward to mate with the lower jaw bone for forming proper occlusal contact between the upper teeth and lower teeth.

BRIEF DESCRIPTION OF THE DRAWINGS

The invention, as well as its many advantages, may be further understood by the following detailed description and drawings in-which.

DETAILED DESCRIPTION OF THE PREFERRED EMBODIMENT

Figure 1:
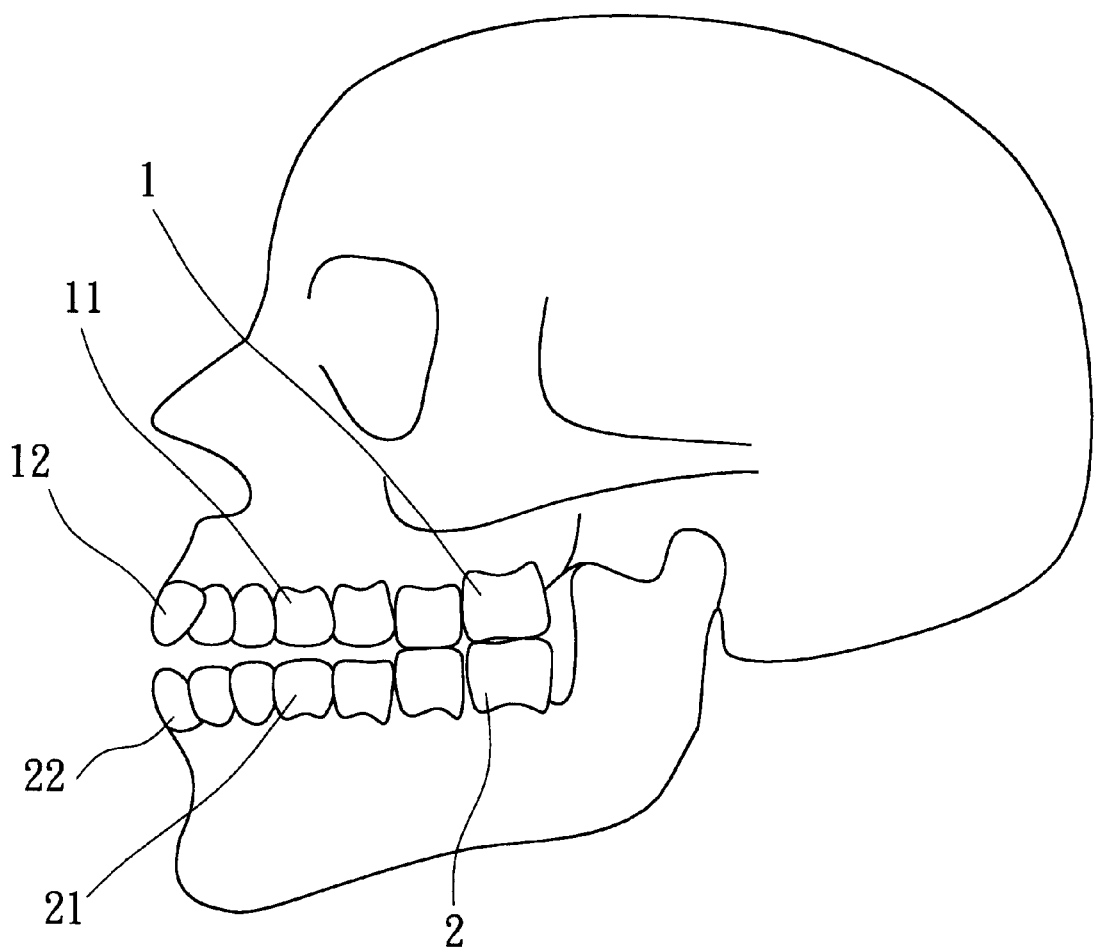
FIG. 1 is a schematic side view of a case of defective occlusion between upper and lower teeth.
Figure 2:
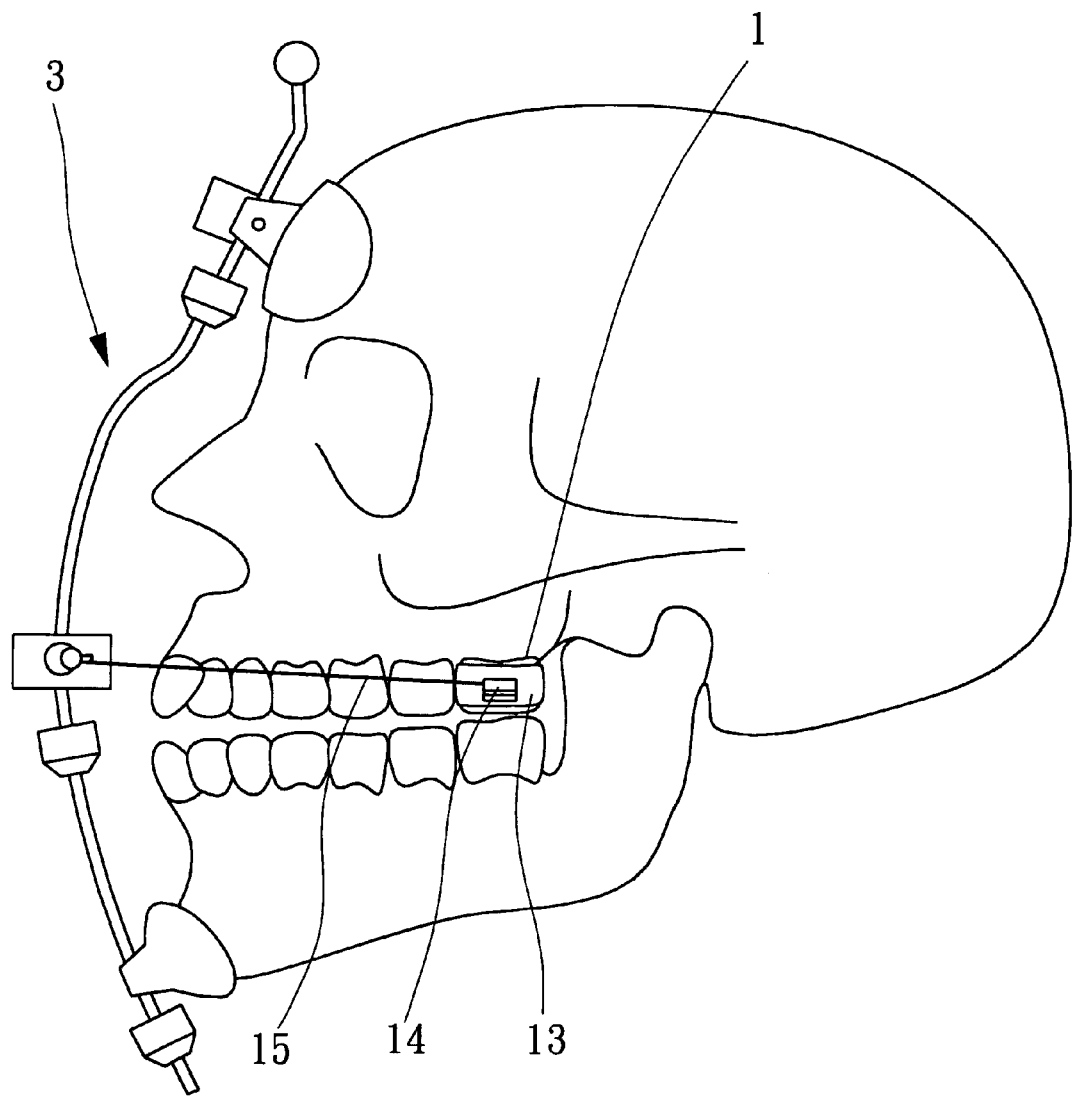
FIG. 2 is a schematic side view of a conventional means for adjusting palatal forward.
Figure 3:
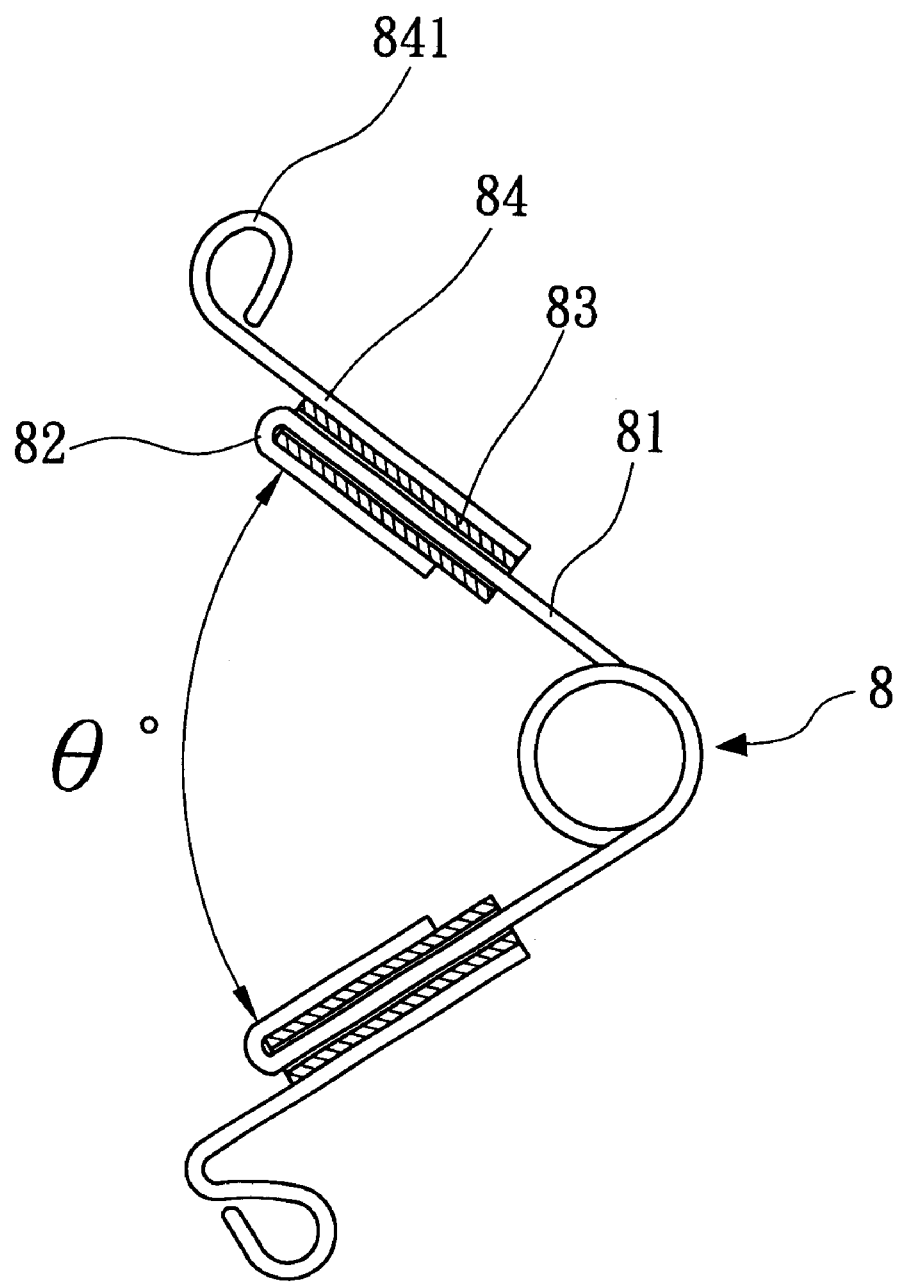
FIG. 3 is a side view of an embodiment of this invention.
Figure 4:
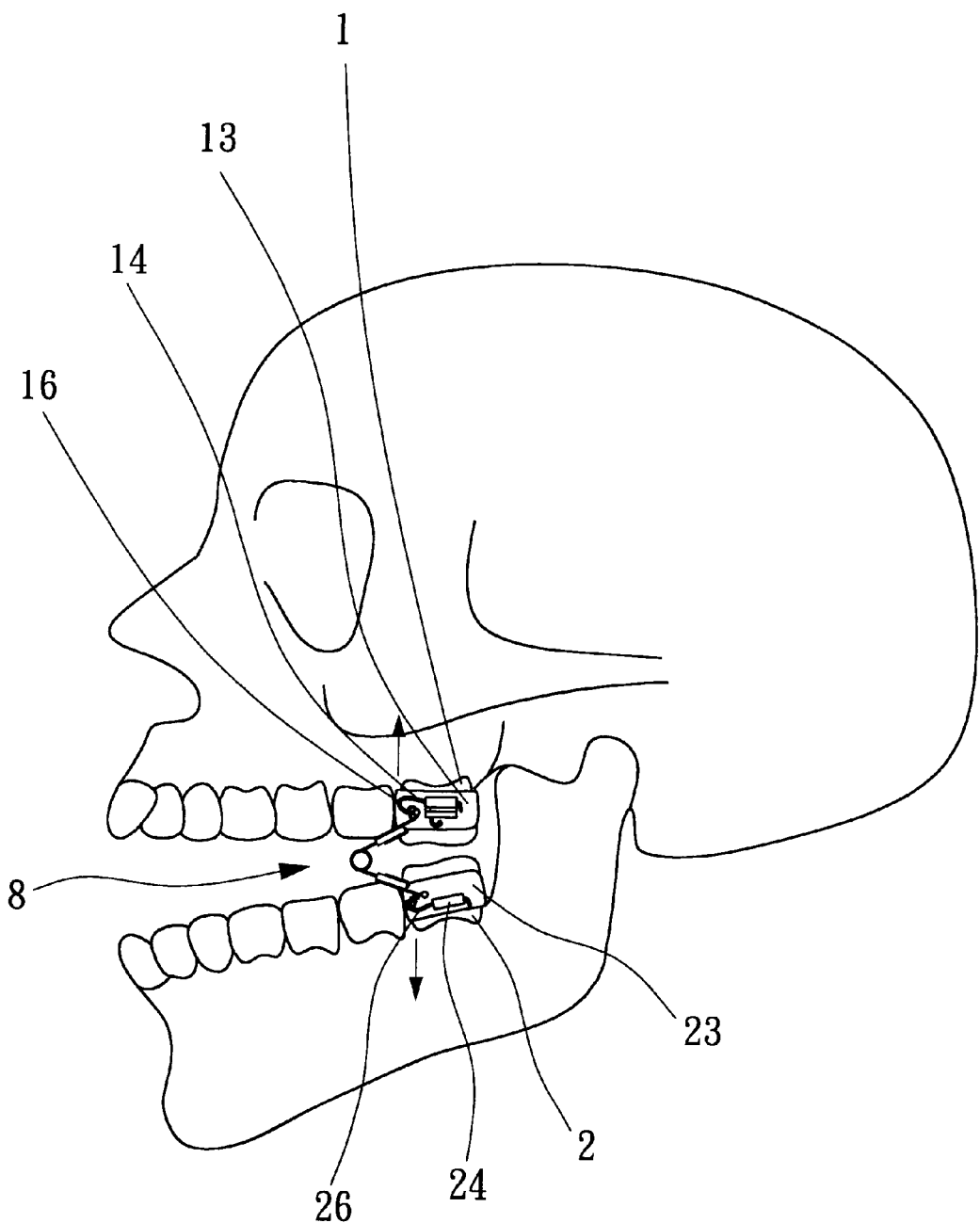
FIG. 4 is a pictorial view of this invention in use.

Referring to FIGS. 3 and 4, this invention includes an elastic means 8, preferable a torsional wire spring, which has two arms 81 forming an angle $\theta°$ which is less than 120°, and preferably less than 90°. Each arm 81 has one end bent over to become a stopped 82. On the arm 81, there is a sleeve 83 movable thereon. There is a latch wire 84 fixedly attached to the sleeve 83. One end of the latch wire 84 is formed like an ear 841.

In the upper jaw, the upper molar 1 has an upper barrel band 13 mounted thereon. On a side wall of the upper barrel band 13, there is an anchor 14 which fastens a steel wire. One end of the steel wire forms an upper hook 16. Following the same principle, the lower molar 2 also has a lower barrel band 23 and a anchor 24 fastened to a steel wire which forms a lower hook 26 at one end thereof.

When in use, the two ears 841 of the elastic means 8 engage respectively with the hooks 16 and 26. When the mouth is closed, the upper molar 1 makes occlusal contact with the lower molar 2, the two arms 81 of the elastic means 8 will be compressed through the steel wire and anchors 14 and 24, and the upper and lower barrel bands 13 and 23. An upward elastic force will be produced by the elastic means 8 on the upper jaw bone. Gradually the upper jaw bone at the molars will be leveled with the rest of upper jaw bone where the premolar, canine and incisors are located and may result in proper occlusal contact between the upper teeth and lower teeth.

The barrel band and elastic means of this invention are simply structured and may be made easily at low cost. There are small size, light weight and may be installed on patient's teeth easily. It may function easily day and night without patient's extra work or effort.

Figure 5:
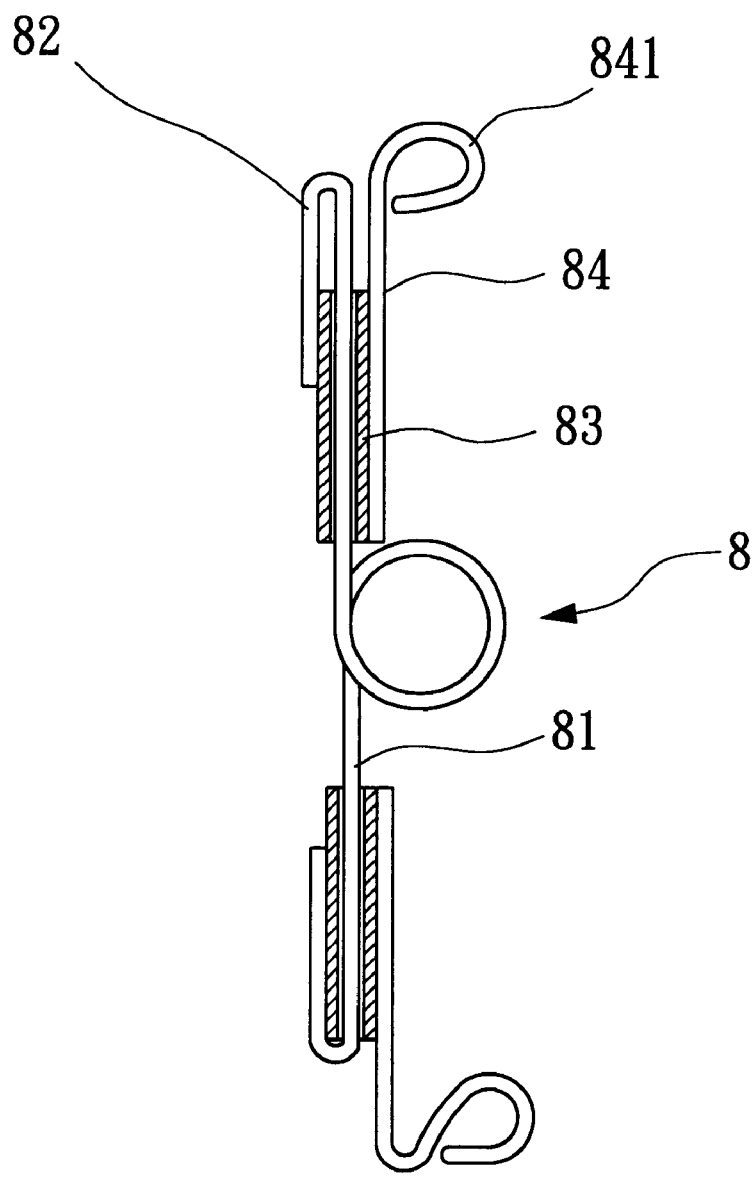
FIG. 5 is a side view of another embodiment of this invention.
Figure 6:
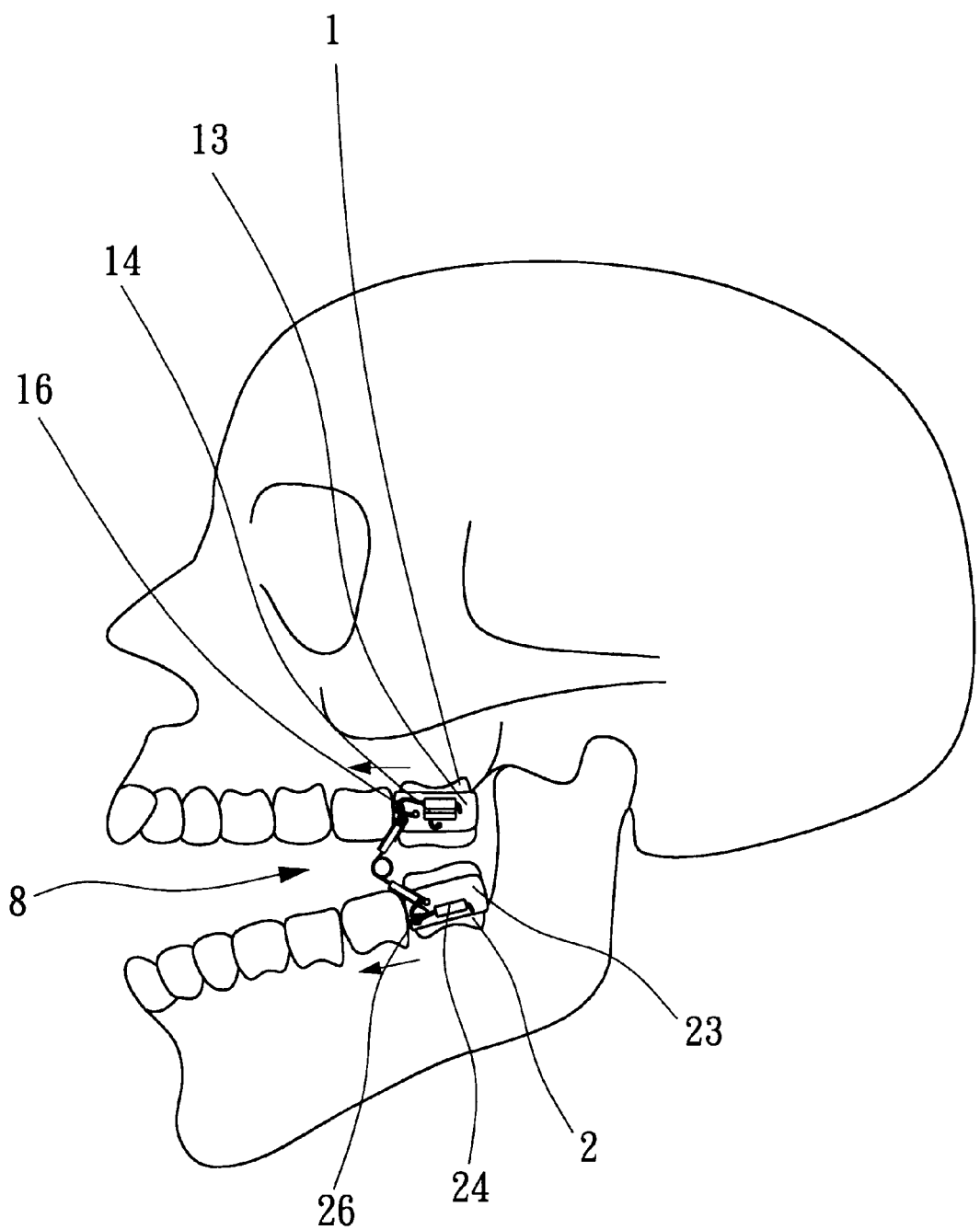
FIG. 6 is a pictorial view of another embodiment of this invention in use.

FIGS. 5 and 6 show another embodiment of this invention. It is generally constructed like the one shown in FIGS. 3 and 4 and have been marked by similar numerals for similar parts. The elastic means 8 is essentially like the one shown in FIG. 3 except that the angle θ° formed between the two arms 81 is greater than 90°, and preferably between 120°~180°. In this preferred embodiment, the two arms 81 are substantially extended in opposite direction linearly (i.e. with the angle θ° becomes 180°). Such that a horizontal pushing force will be provided by the arms 81 when they are compressed toward each other. If the angle between these two arms 81 is less than 120° (or even smaller than 90°), a relatively greater force will occur in a vertical direction but not horizontal.

When in use, the elastic means 8 is compressed and produces a forward dragging force to move the upper barrel band 13 forward. Consequently the upper molar 1 will be moved forward and causes the upper jaw bone and the teeth to move forward to result in proper occlusal contact between the upper and lower teeth. This may be achieved easily and with much less trouble than using conventional facial mask.

It may thus be seen that the objects of the present invention set forth herein, as well as those made apparent from the foregoing description, are efficiently attained, while the preferred embodiments of the invention have been set forth for purpose of disclosure, modifications of the disclosed embodiment of the invention as well as other embodiments thereof may occur the those skilled in the art. Accordingly which do not depart from the spirit and scope of the invention.

What is claimed is:

1. A palatal adjusting device for moving an uneven upper jaw bone upward to produce proper occlusal contact between the upper teeth and lower teeth of a patient, comprising:

an upper barrel band for mounting on an upper molar having a first anchor on a side wall thereof and a first steel wire fastened to the first anchor, the first steel wire having one end formed in a first hook;

a lower barrel band for mounting on a lower molar having a second anchor attached to a side wall thereof and a second steel wire fastened to the second anchor, the second steel wire having one end formed in a second hook; and an elastic means having two arms forming a selected angle less than 120°, each arm forming a stopper at one end and having a sleeve movable thereon, the sleeve having a latch wire attached thereon, the latch wire having an ear at one end thereof;

wherein the ears of the elastic means are respectively engageable with the first and second hook so that the elastic means will be compressed and exerts an upward pressure on the upper barrel band and upper molar when the patient closes mouth.

2. The palatal adjusting device of claim 1, wherein the angle formed by the arms is substantially less than 90°.

3. The palatal adjusting device of claim 1, wherein the elastic means is a torsional wire spring.

4. A palatal adjusting device for moving an uneven upper jaw bone forward to produce proper occlusal contact between the upper teeth and lower teeth of a patient, comprising:

an upper barrel band for mounting on an upper molar having a first anchor on a side wall thereof and a first steel wire fastened to the first anchor, the first steel wire having one end formed in a first hook;

a lower barrel band for mounting on a lower molar having a second anchor attached to a side wall thereof and a second steel wire fastened to the second anchor, the second steel wire having one end formed in a second hook; and an elastic means having two arms forming a selected angle greater than 90°, each arm forming a stopper at one end and having a sleeve movable thereon, the sleeve having a latch wire attached thereon, the latch wire having an ear at one end thereof;

wherein the ears of the elastic means are respectively engageable with the first and second hook so that the elastic means will be compressed and exerts a forward pressure on the upper barrel band and upper molar when the patient closes mouth.

5. The palatal adjusting device of claim 4, wherein the angle is substantially greater than 120°.

6. The palatal adjusting device of claim 4, wherein the angle is substantially one hundred and eighty degree.

7. The palatal adjusting device of claim 4, wherein the elastic means is a torsional wire spring.

* * * * *